United States Patent
Gerold et al.

(10) Patent No.: US 8,871,829 B2
(45) Date of Patent: Oct. 28, 2014

(54) RADIO-OPAQUE MARKER FOR MEDICAL IMPLANTS

(75) Inventors: Bodo Gerold, Zellingen (DE); Claus Harder, Uttenreuth (DE); Bernd Heublein, Hannover (DE); Eva Heublein, legal representative, Coburg (DE); Nora Heublein, legal representative, Cologne (DE); Christoph Heublein, legal representative, Hannover (DE); Heinz Müller, Erlangen (DE)

(73) Assignee: BIOTRONIK VI Patent AG, Baar (CH)

( * ) Notice: Subject to any disclaimer, the term of this patent is extended or adjusted under 35 U.S.C. 154(b) by 721 days.

(21) Appl. No.: 10/596,797

(22) PCT Filed: Sep. 7, 2004

(86) PCT No.: PCT/EP2004/010081
§ 371 (c)(1),
(2), (4) Date: Apr. 26, 2007

(87) PCT Pub. No.: WO2005/065737
PCT Pub. Date: Jul. 21, 2005

(65) Prior Publication Data
US 2007/0191708 A1    Aug. 16, 2007

(30) Foreign Application Priority Data
Dec. 24, 2003  (DE) .................. 103 61 942

(51) Int. Cl.
- *A61F 2/02* (2006.01)
- *A61F 2/82* (2013.01)
- *A61L 31/14* (2006.01)
- *A61L 27/04* (2006.01)
- *A61L 31/18* (2006.01)
- *A61L 27/58* (2006.01)

(52) U.S. Cl.
CPC ......... *A61L 31/18* (2013.01); *A61F 2250/0098* (2013.01); *A61L 31/148* (2013.01); *A61L 27/047* (2013.01); *A61F 2/82* (2013.01); *A61L 27/58* (2013.01)
USPC .... 523/117; 623/1.34; 623/11.11; 623/23.75; 424/422

(58) Field of Classification Search
USPC ............. 523/117; 600/431; 623/1.34, 11.11, 623/23.75; 606/76; 424/422
See application file for complete search history.

(56) References Cited

U.S. PATENT DOCUMENTS

| | | | | |
|---|---|---|---|---|
| 5,725,570 A * | 3/1998 | Heath | | 623/1.2 |
| 5,871,437 A | 2/1999 | Alt | | |
| 6,174,329 B1 * | 1/2001 | Callol et al. | | 623/1.34 |
| 6,174,330 B1 * | 1/2001 | Stinson | | 623/1.34 |
| 6,287,332 B1 * | 9/2001 | Bolz et al. | | 623/1.15 |
| 6,322,588 B1 | 11/2001 | Ogle et al. | | |
| 6,340,367 B1 | 1/2002 | Stinson et al. | | |
| 6,355,058 B1 * | 3/2002 | Pacetti et al. | | 623/1.15 |
| 6,423,085 B1 | 7/2002 | Murayama et al. | | |
| 6,440,487 B1 | 8/2002 | Delfino et al. | | |
| 7,331,993 B2 * | 2/2008 | White | | 623/2.12 |
| 2002/0004060 A1 * | 1/2002 | Heublein et al. | | 424/422 |
| 2002/0040239 A1 | 4/2002 | Murayama et al. | | |
| 2002/0058057 A1 | 5/2002 | Kaplan | | |
| 2002/0103526 A1 * | 8/2002 | Steinke | | 623/1.11 |
| 2002/0138136 A1 | 9/2002 | Chandresekaran et al. | | |
| 2003/0040790 A1 * | 2/2003 | Furst | | 623/1.11 |
| 2003/0072868 A1 * | 4/2003 | Harish et al. | | 427/2.24 |
| 2003/0077200 A1 * | 4/2003 | Craig et al. | | 420/52 |
| 2003/0153971 A1 * | 8/2003 | Chandrasekaran | | 623/1.15 |
| 2003/0153972 A1 * | 8/2003 | Helmus | | 623/1.15 |
| 2003/0199993 A1 | 10/2003 | Gellman et al. | | |
| 2003/0225448 A1 * | 12/2003 | Gerberding | | 623/1.15 |
| 2004/0241036 A1 * | 12/2004 | Meyer-Lindenberg et al. | | 420/405 |
| 2006/0246107 A1 * | 11/2006 | Harder et al. | | 424/426 |

FOREIGN PATENT DOCUMENTS

| | | |
|---|---|---|
| DE | 19754870 A1 | 8/1998 |
| DE | 19718339 A1 | 11/1998 |
| DE | 10044559 A1 | 4/2002 |
| DE | 10128100 A1 | 12/2002 |
| EP | 0 824 900 A2 | 2/1998 |
| EP | 0 894 503 A2 | 2/1999 |
| EP | 0966979 B1 | 12/1999 |
| EP | 1 212 991 A2 | 6/2002 |
| EP | 1270023 A2 | 1/2003 |
| EP | 0 824 900 B1 | 4/2003 |
| WO | WO 99/02195 | 1/1999 |
| WO | WO 99/03515 | 1/1999 |
| WO | WO 99/65537 | 12/1999 |
| WO | WO 02100452 A1 * | 12/2002 |
| WO | WO 2004/043474 A2 | 5/2004 |
| WO | WO 2004/110515 A1 | 12/2004 |

OTHER PUBLICATIONS

El Feninat, F.; Laroche, G.; Fiset, M.; Mantovani, D. Adv. Eng. Mater. 2002, 4, 91-104. Wiley-VCH, 2002.*
Guidoin et al.; Biocompatibility Studies of the Anaconda Stent—Graft and Observations of Nitinol Corrosion Resistance; J. Endovasc Ther; 2004; pp. 385-403; vol. 11; International Society of Endovascular Specialists.
Biocompatibility of Nitinol; Johnson Matthey Medical; downloaded Mar. 1, 2010, from http://jmmedical.com/resources/241/Biocompatibility-of-Nitinol.html.

* cited by examiner

*Primary Examiner* — Michael Pepitone
(74) *Attorney, Agent, or Firm* — Greer, Burns & Crain, Ltd.

(57) ABSTRACT

A radio-opaque marker for medical implants comprising between 10 and 90 weight percent of a biodegradable base component, between 10 and 90 weight percent of one or more radio-opaque elements selected from the consisting of I, Au, Ta, Y, Nb, Mo, Ru, Rh, Ba, La, Ce, Pr, Nd, Sm, Eu, Gd, Tb, Dy, Ho, Er, Tm, Yb, Lu, Hf, Ta, W, Re, Os, Ir and Bi as a marker component and 10 weight percent of residual components, the aforementioned components amounting to 100 weight percent.

18 Claims, No Drawings

RADIO-OPAQUE MARKER FOR MEDICAL IMPLANTS

PRIORITY CLAIM

This patent application is the U.S. National Phase of International Application No. PCT/EP2004/010081, having an International Filing Date of Sep. 7, 2004, which claims priority to German Patent Application No. DE 103 61 942.9, filed Dec. 24, 2003, the disclosures of which are incorporated herein by reference in their entirety.

FIELD OF THE INVENTION

The present invention relates to a radiopaque marker for medical implants and implants having markers of this type.

BACKGROUND OF THE INVENTION

In modern medical technology, implants are used on a continuously increasing degree. The implants are used for supporting vessels, hollow viscera, and vascular systems (endovascular implants), for attaching and temporarily fixing tissue implants and tissue transplants, or even for orthopedic purposes, e.g., as nails, plates, or screws. Frequently, only a temporary support or holding function until completion of the healing process or stabilization of the tissue is required and/or desired. In order to avoid complications which result from the implants remaining permanently in the body, the implants must either be operatively removed again or they are made of a material which is gradually degraded in the body, i.e., biodegradable. The number of biodegradable materials based on polymers or alloys is continuously growing, but in many areas of application, the mechanical properties of a metallic material are still indispensable. In practice, until now only a few metallic materials have proven themselves as biodegradable. At least metal alloys made of magnesium, iron, and tungsten have been suggested.

Inter alia, biodegradable magnesium alloys which are suitable for endovascular and orthopedic implants are known from EP 1 270 023. The alloys may contain up to less than 5 weight-percent rare earths.

However, most biodegradable alloys and polymers for medical implants known from the related art have the disadvantage that they are not detectable or are only detectable to an unsatisfactory extent in current x-ray methods. However, x-ray diagnosis is an important instrument for postoperative monitoring of the healing progress or for checking minimally invasive interventions. Thus, for example, stents have been placed in the coronary arteries during acute myocardial infarction treatment for some years. According to current methods, a catheter which carries the stent in an unexpanded state is positioned in the area of the lesion of the coronary vessel wall. Subsequently, the stent expands either through self-expansive forces or through inflation of a balloon, in order to prevent obstruction of the vessel wall in the expanded state. The procedure of positioning and expanding the stent must be monitored continuously during the procedure through interventional cardiology.

The x-ray visibility of an implant manufactured from a metallic or polymer material is a function of the thickness of the material and, in addition, of the linear extinction coefficient of the material. Iron as a component of medical steels has a linear extinction coefficient of 15.2 KeV/cm, for example, which is typically already insufficient for a contrast-rich monitoring image with the filigree structures of stents. Furthermore, it is known that the linear extinction coefficient becomes greater with increasing atomic number in the periodic system. Thus, for example, gold has a linear extinction coefficient of 101 KeV/cm.

Providing implants with a coating, a strip, or a marker which is incorporated or molded on in another way to improve the x-ray visibility is therefore known. Essentially the following points must be observed for the selection of the marker material:

the marker metal is not to worsen the mechanical properties of implant, in particular by increasing the rigidity,
the marker must be biocompatible, and
the marker may not flake or crack off during the implantation, in particular during the expansion or placement of a stent.

Known marker methods provide attaching metal strips made of gold or other noble metals in specific areas of the stent, for example. Metal strips of this type may loosen, shift, or even fall off, however. A non-degradable marker made of a noble metal causes the expectation of the formation of a local element with the usually non-noble metals of the main body of implant, through which the marker itself may be resolved very rapidly from the structure. However, when the marker is dissolved very rapidly, this may also occur before the complete endothelialization; the marker may then float away and result in an embolization. Furthermore, there is the danger of abrasion of the intima during positioning of the implant.

With metal coating methods, radiopaque marking areas may be applied to the implants through chemical or physical vacuum deposition (CVD or PVD). Alternatively, methods such as ion beam assisted deposition (IBAD) and microfusion are suitable, using which very homogeneous coatings in the micrometer range are producible on the implant surface.

The application of marker layers and the positioning of marker elements on the implants made of biodegradable alloys or polymers are anything but trivial and typically requires individual tailoring of the material properties of the marker element to the further materials used in the implant and also adaptations in the design of the implant. Known attempted achievements of the object may therefore not be transferred without further steps to new materials, in particular the promising biodegradable alloys and polymers. Furthermore, the marker element itself is to be at least largely biodegradable or is at least to be converted into physiologically harmless components. These are understood as components which have dimensions significantly smaller than the dimensions of the marker before implantation, but which are not degraded further and are intercalated in the body in unchanged form.

SUMMARY OF THE INVENTION

It is a feature of the present invention to provide an at least partially biodegradable marker having a sufficient x-ray visibility.

A further feature of the present invention is to specify suitable implants for at least partially biodegradable markers.

According to a first aspect of the present invention, a feature of interest is achieved by a radiopaque marker for medical implants containing:

10 to 90 weight-percent of a biodegradable base component,
10 to 90 weight-percent of one more radiopaque elements selected from the group consisting of I, Au, Ta, Y, Nb, Mo, Ru, Rh, Ba, La, Ce, Pr, Nd, Sm, Eu, Gd, Tb, Dy, Ho, Er, Tm, Yb, Lu, Hf, Ta, W, Re, Os, Ir, and Bi as marker components, and less than or equal to 10 weight-percent residual components, The components cited adding up to 100 weight-percent. The proportions of the components are weighted in this case in such way that the marker is still at least partially biodegradable, but there is nonetheless adequate x-ray visibility at normal dimensioning of the medical implant.

Biodegradability in the meaning according to the present invention is understood as at least partial degradation of the marker in the living organism occurring over time due to chemical, thermal, oxidative, mechanical, or biological processes. The degradation relates at least to the base component of the marker. The marker component is either biodegradable in turn or is provided as a finely divided powder after complete degradation of the base component, which may be excreted from the body without problems or is intercalated in the tissue without noticeable further biological interaction. In other words, the possibly remaining nonbiodegradable components of the marker component do not form a closed structure per se, but rather disintegrate into smaller components. Therefore, the marker component is to be evaluated and adapted in this direction through in vitro degradation experiments if necessary.

An exemplary embodiment of the marker is an alloy which particularly contains one or more biodegradable elements selected from the group consisting of magnesium, iron, and zinc as the base component. These alloys offer the advantage above all that the material properties of alloys are clearly adapted to one another in comparison to typical biodegradable alloys, in particular magnesium alloys. The manufacturing of implants having marker elements, which are based on a combination of typical biodegradable metallic alloys as the main body with the radiopaque alloy according to the present invention as the marker, is thus simplified. The phase boundary tensions which otherwise typically frequently occur precisely at the phase boundaries between marker and main body of implant may be reduced because of the adaptation of the material properties. The formation of local elements in heterogeneous alloys between the often noble marker components and the non-noble base components represents a desired effect which accelerates the decomposition of the marker.

In an alternative exemplary embodiment to the above-mentioned alloy, the marker is a composite having a biodegradable alloy as the base component. The base component is again gradually degraded in the above-mentioned way, through which the marker loses its original mechanical integrity. The further components are either also resorbed or intercalated in particle form in the tissue. Furthermore, it is preferable for the biodegradable polymer of the composite to comprise hyaluronic acid, chitosan, and polylactides, the polymers cited being able to be provided as derivatives which may be derived from the basic structure if necessary. The polymers cited appear to be especially suitable, since their in vitro degradation may be controlled through targeted derivatization, outstandingly good biocompatibility is provided, the processing may be performed according to known methods, and the degradation products at least partially exert a positive physiological effect on the surrounding tissue.

The term "base component" in the meaning of the present invention also includes any type of combination of the cited materials and further materials capable of biodegradation, of course. Thus, the base component may be a mixture of multiple biodegradable polymers and/or alloys. The shared feature of all these conceivable base component is the absolute requirement of the simultaneous presence of a marker component.

According to a preferred exemplary embodiment of the present invention, which may also be implemented in combination with the above-mentioned special exemplary embodiments of the marker as an alloy or composite, the marker component comprises one or more elements selected from the group consisting of I, Ta, Y, Ce, Nd, Sm, Gd, and Dy. The elements cited are distinguished by their outstanding biocompatibility, favorable linear extinction coefficient, and good availability. In particular, a marker component which entirely or at least 90 weight-percent or more of the marker component comprises tantalum is especially preferred. Tantalum has been shown to be especially biocompatible and easily processable and may particularly be a component of the marker in the form of extremely small metal balls having a diameter of a few micrometers. In addition, if Y, Ce, Nd, Sm, Gd, or Dy are used, magnesium alloys become more heat resistant and may be processed better. The elements Y and Nd have additionally shown in the effect of inhibiting the proliferation of smooth human muscle cells in initial cell culture experiments, so that the use of these elements appears especially advisable in connection with endovascular implants, such as coronary stents.

The proportion of the base component in the marker is preferably 30 to 70 weight-percent, in particular 40 to 60 weight-percent. In this way, an extensive disintegration of the marker may be ensured, but good x-ray visibility may additionally be ensured.

Furthermore, it is preferable for a proportion of the rare earth metals, including yttrium, as components of the marker component, to be not more than 20 weight-percent, in particular not more than 15 weight-percent, in the marker. In this way, it may be ensured that the toxicity at least partially existing at higher doses of the metals cited cannot result in formation of necrosis in the surrounding tissue.

The residual components comprise inorganic or organic fillers, auxiliary materials, or residual materials, which are provided without restrictions of the functionality of the marker, e.g., because of impurities of the starting materials, but also for improved processing of the individual components. The proportion of the residual components in the marker is preferably less than or equal to 5 weight-percent, in particular less than or equal to 1 weight-percent. It is conceivable for the residual component to be a pharmacologically active ingredient which improves the tissue compatibility, for example.

According to a second aspect of the present invention, a feature of interest is achieved by a self-biodegradable implant which contains at least one section which comprises the marker according to the present invention. The main body of the implant is molded from a biodegradable material which is synthesized on the basis of a polymer or metal, for example. It is conceivable and especially preferable for the main body of implant to be produced entirely or in parts from the marker. Alternatively, the main body may be coated with the marker. In the first variation, markers based on an alloy are preferred, since these frequently fulfill the mechanical requirements of the material better. An example of this is coronary stents made of biodegradable magnesium, iron, or tungsten compounds. In case of coating with the marker, coating thicknesses in the range from approximately 5 to 100 µm are preferred, since these ensure adequate x-ray visibility, but do not restrict the functionality of the coated main body. According to an advantageous exemplary embodiment, the coating is only applied terminally to the implant, e.g., through coating using a mask.

The implant is preferably at least partially molded from a biodegradable magnesium alloy known from the related art. In this case, an alloy whose base component is also magnesium is preferred as the marker. In this way, the material properties of the main body and of the marker are adapted to one another. Implants made of known magnesium alloys may therefore be coated especially well with the alloy of the marker according to the present invention or may be implemented in molded partial areas. The material similarity increases the adhesion between the different alloys, so that flaking or cracking of the coating or a fracture along the phase boundaries between the marker alloy and the known magnesium alloys of the main body in the event of mechanical strain is avoided. Because of the very similar properties, it is generally not necessary to rework a basic stent design for applying or introducing the marker alloy, for example.

The at least largely biodegradable implant is preferably an endovascular implant, in particular a stent or an occluder. Furthermore, the marker according to the present invention, in particular in the form of an alloy, is preferably used in orthopedic implants, such as nails, screws, clips, or alloplastic prostheses, such as anastomosis implants in the form of a small tube for connecting two vessel ends.

The present invention is explained in greater detail in the following in exemplary embodiments.

A stent of typical construction having a main frame made of the biodegradable magnesium alloy WE43 (composition: Y 4.1 weight-percent; Nd 2.2 weight-percent; Zr 0.5 weight-percent; other less than 0.4 weight-percent and remainder Mg) is bonded to a marker in different ways in the following.

According to a first variation, the marker comprises a coating deposited from a Mg/Y target through PVD. The Mg/Y target has a composition of approximately 85 weight-percent magnesium and 15 weight-percent yttrium, for example. Of course, the elements for the base and marker components may be varied depending on the desired composition of the marker to be deposited. Deposition methods of this type are well-known to those skilled in the art, so that more detailed description will be dispensed with. The deposition method is controlled in this case in such a way that an approximately 5 to 100 μm thick layer of the marker results. If desired, the deposition location may be locally delimited by focusing the material beam or masking, e.g., to produce a terminal circular marker.

According to an alternative variation, the surface of implant may be covered by a composite made of a biodegradable polymer base component and a marker component. This may be performed, for example, by adding tiny tantalum or gadolinium balls acting as marker components to a polymer, based on polymerized hyaluronic acid, acting as a base component. The resulting dispersion is subsequently applied to the implant through common immersion or spraying methods and dried. A weight of the dried polymerized hyaluronic acid to the weight of the tantalum or gadolinium balls is approximately 50-50, for example. The marker may be introduced in a locally delimited way, e.g., in cavities in the main body of implant provided for this purpose, or may cover the entire implant as a coating.

The invention claimed is:

1. A radiopaque marker for medical implants comprising:
a) 10 to 90 weight-percent of a biodegradable base component consisting essentially of an alloy and capable of degrading in situ over a medically useful period of time;
b) 10 to 90 weight-percent of a marker component comprising one or more radiopaque elements selected from the group consisting of I, Au, Ta, Y, Nb, Mo, Ru, Rh, Ba, La, Ce, Pr, Nd, Sm, Eu, Gd, Tb, Dy, Ho, Er, Tm, Yb, Lu, Hf, W, Re, Os, Ir, and Bi, wherein the radiopaque elements comprise at lest 90 weight-percent Ta, the marker component comprising fine particles; and,
c) less than or equal to 10 weight-percent residual components,
the components cited adding up to 100 weight-percent, wherein as the base component degrades the marker component particles are excreted without appreciable absorption into surrounding tissue.

2. The marker of claim 1, wherein the biodegradable base component consists essentially of one or more biodegradable elements selected from the group consisting of magnesium, iron, and zinc.

3. The marker of claim 1, wherein the marker component comprises one or more elements selected from the group consisting of I, Ta, Y, Ce, Nd, Sm, Gd, and Dy.

4. The marker of claim 1, wherein a proportion of the radiopaque elements Y, La, Ce, Pr, Nd, Sm, Eu, Gd, Tb, Dy, Ho, Er, Tm, Yb, and Lu as components of the marker component is not more than 10 weight-percent in the marker.

5. A biodegradable implant having a section or coating incorporating a radiopaque marker, the section or coating incorporating the radiopaque marker comprising:
a) 30 to 70 weight-percent of a base component consisting essentially of a biodegradable alloy capable of degrading in situ over a medically useful period of time;
b) 30 to 70 weight-percent of a marker component comprising one or more radiopaque elements selected from the group consisting of I, Au, Ta, Y, Nb, Mo, Ru, Rh, Ba, La, Ce, Pr, Nd, Sm, Eu, Gd, Tb, Dy, Ho, Er, Tm, Yb, Lu, Hf, W, Re, Os, Ir, and Bi, wherein the radiopaque elements comprise at least 90 weight-percent Ta, the marker component comprising fine particles; and,
c) less than or equal to 10 weight-percent residual components,
the components cited adding up to 100 weight-percent wherein as the base component degrades the marker component particles are excreted without appreciable absorption into surrounding tissue.

6. A biodegradable implant comprising:
a) a main body; and
b) a radiopaque marker at least partially comprising the main body, the radiopaque marker comprising
(i) 10 to 90 weight-percent of a base component consisting essentially of a biodegradable alloy;
(ii) 10 to 90 weight-percent of one or more radiopaque elements selected from the group consisting of I, Au, Ta, Y, Nb, Mo, Ru, Rh, Ba, La, Ce, Pr, Nd, Sm, Eu, Gd, Tb, Dy, Ho, Er, Tm, Yb, Lu, Hf, W, re, Os, Ir, and Bi, wherein the radiopaque elements comprise at least 90 weight-percent Ta, the marker component comprising fine particles; and,
(iii) less than or equal to 10 weight-percent residual components, the components cited adding up to 100 weight-percent wherein as the base component degrades the marker component particles are excreted without appreciable absorption into surrounding tissue.

7. The marker of claim 1, wherein a proportion of the rare earth elements and of yttrium as components of the marker component is less than or equal to 10 weight-percent, in the marker.

8. The marker of claim 6, wherein the implant has a plurality of cavities formed therein and the radiopaque marker is at least partially disposed within the cavities.

9. The marker of claim 1, wherein the fine particles, when dispersed in situ, are in contact with body material.

10. The marker of claim 1 wherein the base component is present in an amount of 40 to 60 weight-percent.

11. The implant of claim 5 wherein the radiopaque marker is a coating.

12. The implant of claim 11 wherein the coating has a thickness in a range of approximately 5 μm to 100 μm.

13. The implant of claim 11 wherein the coating is applied terminally to the implant.

14. The implant of claim 5 wherein the base component is present in an amount of 30 to 70 weight-percent.

15. The implant of claim 6 wherein the base component is present in an amount of 30 to 70 weight-percent.

16. A radiopaque marker for medical implants comprising:
   a) 10 to 90 weight-percent of a biodegradable base component consisting essentially of an alloy and capable of degrading in situ over a medically useful period of time;
   b) 10 to 90 weight-percent of a marker component comprising at least 90 weight-percent of Ta, the marker component comprising fine particles; and,
   c) less than or equal to 10 weight-percent residual components, the components cited adding up to 100 weight-percent, wherein as the base component degrades the marker component particles are excreted without appreciable absorption into surrounding tissue.

17. A biodegradable implant having a section or coating incorporating a radiopaque marker, the section or coating incorporating the radiopaque marker comprising:
   a) 10 to 90 weight-percent of a base component consisting essentially of a biodegradable alloy capable of degrading in situ over a medically useful period of time;
   b) 10 to 90 weight-percent of a marker component comprising at least 90 weight-percent of Ta, the marker component comprising fine particles; and,
   c) less than or equal to 10 weight-percent residual components, the components cited adding up to 100 weight-percent wherein as the base component degrades the marker component particles are excreted without appreciable absorption into surrounding tissue.

18. A biodegradable implant comprising:
   a) a main body; and
   b) a radiopaque marker at least partially comprising the main body, the radiopaque marker comprising
      (i) 10 to 90 weight-percent of a base component consisting essentially of a biodegradable alloy;
      (ii) 10 to 90 weight-percent of one or more radiopaque elements wherein the radiopaque elements comprise at least 90 weight-percent Ta, the marker component comprising fine particles; and,
      (iii) less than or equal to 10 weight-percent residual components, the components cited adding up to 100 weight-percent wherein as the base component degrades the marker component particles are excreted without appreciable absorption into surrounding tissue.

* * * * *